United States Patent
Bianchini et al.

(10) Patent No.: US 6,916,931 B2
(45) Date of Patent: Jul. 12, 2005

(54) TRIDENTATE LIGANDS AND RELATIVE COMPLEXES WITH TRANSITION METALS

(75) Inventors: Claudio Bianchini, Florence (IT); Anna Sommazzi, Santa Margherita Ligure (IT); Giuseppe Mantovani, Finale Emilia (IT); Roberto Santi, Novara (IT); Francesco Masi, Sant'Angelo Lodigiano (IT)

(73) Assignee: Polimeri Europa S.p.A., Brindisi (IT)

( * ) Notice: Subject to any disclaimer, the term of this patent is extended or adjusted under 35 U.S.C. 154(b) by 0 days.

(21) Appl. No.: 10/399,983
(22) PCT Filed: Oct. 4, 2001
(86) PCT No.: PCT/EP01/11482
§ 371 (c)(1), (2), (4) Date: Oct. 14, 2003
(87) PCT Pub. No.: WO02/34746
PCT Pub. Date: May 2, 2002

(65) Prior Publication Data
US 2004/0087788 A1 May 6, 2004

(30) Foreign Application Priority Data
Oct. 26, 2000 (IT) .................................. MI2000A2321

(51) Int. Cl.⁷ ............................................ C07D 409/04
(52) U.S. Cl. .................................................. 546/280.4
(58) Field of Search ...................................... 546/280.4

(56) References Cited
PUBLICATIONS

S.D. Ittel et al. Chemical Reviews, vol. 100, No. 4, pp. 1169–1203 2000.

*Primary Examiner*—Patricia L. Morris
(74) *Attorney, Agent, or Firm*—Oblon, Spivak, McClelland, Maier & Neustadt, P.C.

(57) ABSTRACT

The present invention relates to tridentate ligands and the relative complexes of these ligands with transition metals. The ligands and their complexes are useful in the oligomerization and/or polymerization of ethylene and α-olefins. The ligands are represented by formula (I)

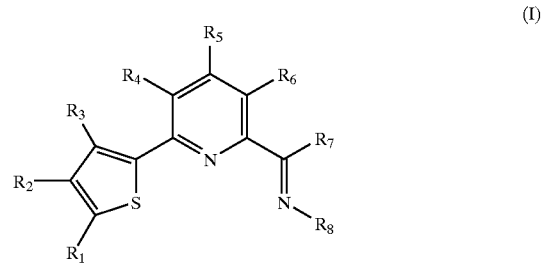

wherein $R_1$ is ethyl, $R_2$, $R_3$, $R_4$, $R_5$ and $R_6$, are independently selected from the group consisting of hydrogen, halogen, $C_1$–$C_{10}$ alkyl, $C_6$–$C_{15}$ aryl, and halogenated $C_6$–$C_{15}$ aryl; $R_7$ is selected from the group consisting of H, $C_1$–$C_{10}$ alkyl, and $C_6$–$C_{15}$ aryl; and $R_8$ is selected from the group consisting of phenyl, alkyl substituted phenyl, $C_1$–$C_{10}$ alkyl and $C_6$–$C_{15}$ aryl.

9 Claims, No Drawings

TRIDENTATE LIGANDS AND RELATIVE COMPLEXES WITH TRANSITION METALS

The present invention relates to new tridentate ligands and the relative complexes with transition metals.

It is generally known in the art that ethylene, or α-olefins in general, can be oligomerized, polymerized or copolymerized by means of low, medium or high pressure processes, with heterogeneous catalysts based on a transition metal of groups 4 to 6 of the periodic table of elements (in the form approved of by IUPAC and published by "CRC Press Inc." in 1989, to which reference will be made hereafter with the term "periodic table"), generally known as Ziegler-Natta type catalysts. A more recent group of catalysts active in the polymerization of α-olefins consists of the combination of an oligomeric organo-oxygenated derivative of aluminum (in particular methylaluminoxane or MAO) with an $\eta^5$-cyclopentadienyl compound (metallocene) of a transition metal of the same groups 4 to 6 of the periodic table, and especially group groups 4 to 6 of the periodic table, and especially group 4. These latter catalysts are substantially soluble in hydrocarbon solvents and for this reason are often defined as "homogeneous", even if they are sometimes used in heterogeneous form by supporting them on an inert solid material. The characteristics of polymerization processes based on this type of catalytic systems can substantially differ from those of processes using heterogeneous catalysts of the Ziegler-Natta type, to such an extent that new olefinic polymers can be obtained, in certain cases, which could not be prepared with the traditional systems. Among the numerous publications available in literature on the matter, reference is made, for example, to the publications "Progress in Polymer Science", vol. 20 (1995), pages 309–367, and "Journal of Molecular Catalysis A: Chemical", vol. 128 (1998), pages 1–331, for a wide range of applications of the above techniques and results obtained.

In the continuous attempt to improve the state of the art, new catalysis methods have been recently proposed for the oligo-/polymerization of α-olefins based on complexes of "heavy" transition metals, i.e. of groups 8 to 10 of the periodic table.

Finally, studies are being increasingly more directed towards catalysts consisting of transition metals complexed with nitrogenated chelating ligands useful for both the polymerization of ethylene and for its copolymerization with alpha-olefins and with polar comonomers. A recent review on the subject is provided in Chemical Reviews, 2000 (Steven D. Ittel, Lynda K. Johnson, Vol. 100, Nr. 4, pages 1169–1203).

A new group of ligands has now been found, together with the relative complexes with transition metals useful in the oligomerization and/or polymerization of ethylene and α-olefins.

In accordance with this, the present invention relates to ligands having general formula (I)

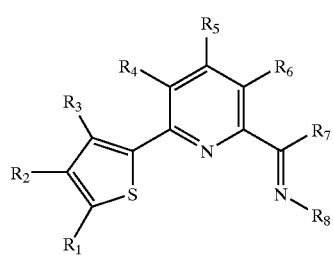

(I)

wherein $R_1$, $R_2$, $R_3$, $R_4$, $R_5$ and $R_6$, the same or different, are selected from hydrogen, halogen, $C_1$–$C_{10}$ alkyl, $C_6$–$C_{15}$ aryl optionally halogenated, or adjacent pairs of $R_i$ groups (with i ranging from 1 to 6) are bound to each other to give cyclic hydrocarbon structures condensed with the thiophene or pyridine ring;

$R_7$ is selected from H, $C_2$–$C_{10}$ alkyl, $C_6$–$C_{15}$; aryl;

$R_8$ is selected from $C_1$–$C_{10}$ alkyl and $C_6$–$C_{15}$ aryl.

In the preferred embodiment, $R_3$, $R_4$, $R_5$, $R_6$, $R_7$ are selected from H and $C_1$–$C_{10}$ alkyl radicals, $R_8$ is a $C_6$–$C_{15}$ aryl radical.

In the even more preferred embodiment, $R_3=R_4=R_5=R_6=$H, $R_7=C_1$–$C_{10}$ alkyl; $R_8$=phenyl as such or alkyl substituted.

More specifically, an object of the present invention relates to:

**) a ligand having general formula (I) wherein $R_1=R_2=R_3=R_4=R_5=R_6$=H; $R_7=CH_3$; $R_8$=2,6-diisopropylphenyl;

**) a ligand having general formula (I) wherein $R_1=C_2H_5$; $R_2=R_3=R_4=R_5=R_6$=H; $R_7=CH_3$; $R_8$=2,6-diisopropylphenyl;

**) a ligand having general formula (I) wherein $R_1$=9-anthryl; $R_2=R_3=R_4=R_5=R_6$=H; $R_7=CH_3$; $R_8$=2,6-diisopropylphenyl;

**) a ligand having general formula (I) wherein $(R_1-R_2)$=—(—CH=)$_4$—; $R_3=R_4=R_5=R_6$=H; $R_7=CH_3$; $R_8$=2,6-diisopropylphenyl;

The compounds having general formula (I) can be obtained according to the process described in scheme (S).

SCHEME S

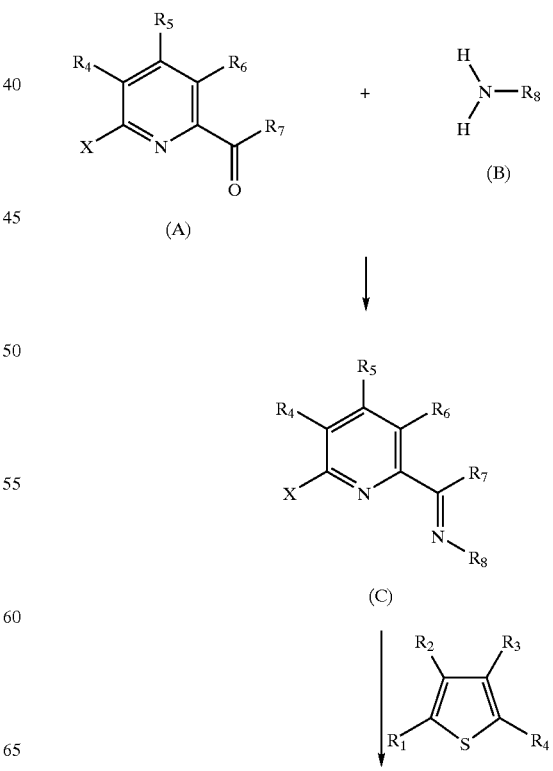

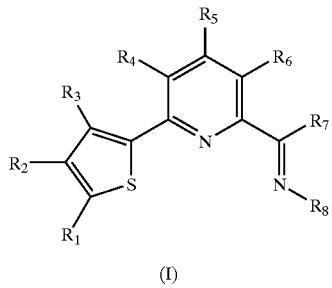

(I)

In accordance with this, the present invention relates to a process for the preparation of ligands having general formula (I) which comprises:

i) a first step which consists in the condensation of halogen acyl-pyridine having general formula (A),

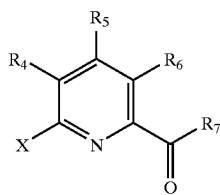

(A)

wherein X is a halogen, preferably bromine, $R_4$, $R_5$, $R_6$ and $R_7$ having the meaning defined above, with the primary amine, preferably aromatic, having general formula (B),

(B)

wherein $R_8$ has the meaning indicated above, to give the halogen imino-pyridine having general formula (C);

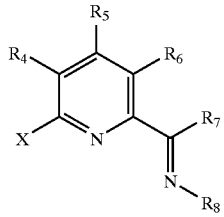

(C)

ii) a second step which consists in the reaction of the halogen imino-pyridine having general formula (C) with the thiophene derivative having general formula (D), wherein $R_1$, $R_2$, $R_3$ have the meaning defined above and $R_9$ is an organometallic radical bound to the thiophene ring

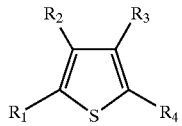

(D)

thus obtaining the compound having general formula (I) object of the present invention.

As far as the halogen acyl-pyridine having general formula (A) is concerned, this can be prepared according to techniques known to experts in the field. In particular, the synthesis of compounds (A) is described by Parks, J. E. et al.; J. Organomet. Chem., 56, 53–66 (1973) and by Peterson M. A. et al.; J. Org. Chem., 62, 23, 8237–8239 (1997). The bromine acyl-pyridine (compound having general formula I wherein X=Br, $R_4$=$R_5$=$R_6$=H; $R_7$=$CH_3$) can be typically prepared, see the experimental part, by the reaction of 2,6-dibromine pyridine with N,N-dimethyl acetamide in the presence of Lithium butyl.

With respect to step (i) of the process of the present invention, this consists in the condensation, well known to experts in the field, of an acetyl derivative with a primary amine, preferably aromatic ($R_8$=phenyl or mono or polyalkyl substituted phenyl). The condensation is typically effected in mass, i.e. without a solvent, preferably in the presence of an excess of amine, at temperatures higher than 100° C., thus favouring the removal of the water formed as by-product. At the end of step (i) the halogen imino-pyridine (C) is obtained.

Step (ii) of the process of the present invention consists in the reaction of the halogen imino-pyridine having general formula (C) with the thiophene derivative having general formula (D). In the preferred embodiment $R_3$ is an organometallic radical selected from alkyl derivatives of tin or other metals such as Li, Mg, Zn, Hg, preferably tin.

Step (ii) consists in the reaction of halogen imino-pyridine (C), preferably bromine imino-pyridine, with the thiophene derivative (D), directly or in the presence of catalysts, for example palladium tetrakis-triphenyl-phosphine. The reaction produces the ligand having general formula (I).

The present invention also relates to complexes having general formula (II)

$$(L)M(Y)_n \qquad (II)$$

wherein

L represents the ligand having general formula (I),

M is a metal selected from transition metals, i.e. metals of groups 3 to 12, preferably from 4 to 10, of the periodic table, and lanthanides; the above metal M being in oxidation state "s" positive different from zero, generally between 1 and 4;

Y is selected from groups of an anionic nature bound to the metal as anion in ionic couple or with a covalent bond of the "σ" type;

n expresses the number of Y groups sufficient for neutralizing the formal oxidation charge "s" of the metal M.

Typical but non-limiting examples of complexes having general formula (II) are indicated in the experimental part.

In the preferred embodiment of the present invention, M is selected from metals of groups 4 to 10 of the periodic table. Even more preferably, M is selected from metals of groups 8 and 9, particularly Cobalt, Iron, Ruthenium, Rhodium, Iridium in oxidation states from +2 to +3. Cobalt and Iron in oxidation state +2 are particularly suitable.

The symbol Y in formula (II) indicates groups (or ligands) of an ionic nature of the complex claimed. It is known that transition metals and lanthanides rarely form compounds and complexes of an exclusively ionic nature, the bond between metal and ligand being of an ionic-covalent nature or totally covalent, in some cases. The symbol Y in formula (II) therefore relates to ligands of an anionic nature, which are normally bound to the metal M with a bond of a mainly covalent nature. The term $(Y)_n$ generally indicates the combination of ligands of an anionic nature, regardless of the actual number and type of Y present in the compound having formula (II). Y ligands different from each other are included in the above definition. Polyvalent or polydentate $(Y)_n$ ligands, for example oxalate, sulfate, phthalate groups, are also included in the scope of the present invention.

Examples of groups of $(Y)_n$ ligands of an anionic nature which can form compounds having formula (II) are halides, especially chloride and bromide, sulfates, and acid sulfates, alkyl- and aryl-sulfonic groups, phosphates and polyphosphates, alkyl- and aryl-phosphonic groups, hydride, linear, cyclic or branched alkyl groups having from 1 to 15 carbon atoms, such as methyl, ethyl, butyl, isopropyl, isoamyl, octyl, decyl, benzyl, cyclopentyl, cyclohexyl, 4-methylcyclohexyl, alkylsilyl groups having from 1 to 20 carbon atoms, such as, for example, trimethylsilyl, triethylsilyl or tributylsilyl, aryl groups having from 6 to 15 carbon atoms, such as phenyl or toluyl, alkoxyl or thioalkoxyl groups having from 1 to 10 carbon atoms, such as methoxyl, ethoxyl, iso- or secbutoxyl, ethylsulfide, carboxylate or dicarboxylate groups, such as acetate, trifluoroacetate, propionate, butyrate, pivalate, stearate, benzoate, oxalate, malonate, phthalate, or again, a dialkylamide group having from 2 to 15 carbon atoms, such as diethylamide, dibutylamide, or alkylsilylamide, such as bis(trimethylsilyl) amide or ethyltrimethylsilylamide, divalent organic groups such as the trimethylene or tetramethylene group, or the ethylenedioxy group.

Groups or ligands different from each other can also be present, if desired, such as, for example, a chloride and a carboxylate or alkoxide group. The Y groups can be selected so as to make the complex having formula (II) sufficiently soluble in the solvents used during the oligo- or polymerization process of ethylene, especially in the case of processes in solution.

In certain cases however the solubility of the complex is irrelevant, as in the case of supported complexes. In this latter case, the group of an anionic nature (Y) may also have an anionic function chemically bound to the carrier. Examples of supported complexes and their preparation are provided in the experimental part.

A further object of the present invention relates to a process for preparing complexes having general formula (II) which comprises putting the ligand L having general formula (I) in contact with a salt of the selected metal M, wherein M has the meaning defined above, preferably in the presence of an inert liquid.

For example, it is possible to start from the salt of the metal M dissolved in an inert solvent (for example an alcohol or an ether). The stoichiometric quantity of the ligand L is added to this solution. The complex thus formed can be separated according to techniques known to experts in the field, for example crystallization or precipitation by means of a non-solvent, and subsequent separation by filtration or decanting. The above complex is usually formed rapidly and in more or less quantitative yields already under bland temperature conditions.

The complex having general formula (II) can also be prepared in situ, without previous isolation.

The reaction is schematically as follows:

$$M(Y)_n + L \rightarrow LM(Y)_n$$

For simplicity of production and conservation of the respective complexes, the chlorine, bromine, alkoxide and carboxylate groups (having from 2 to 15 carbon atoms) are preferred Y groups.

The following examples are provided for a better understanding of the present invention.

EXAMPLES

Example 1

Synthesis of the Ligand Having General Formula (I) Called (BL16)

This synthesis is carried out starting from benzothiophene according to scheme 1.

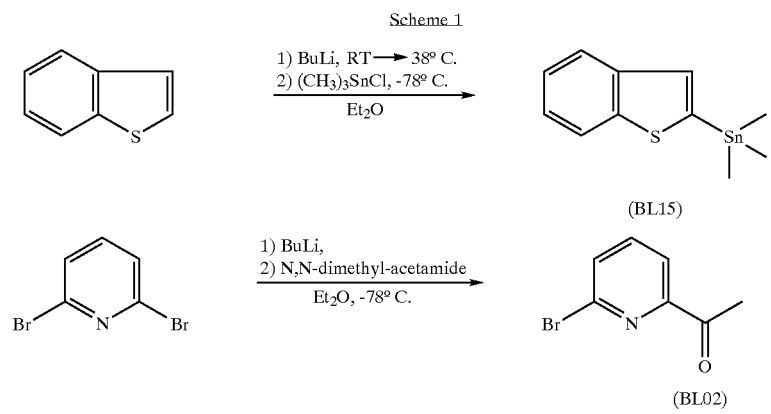

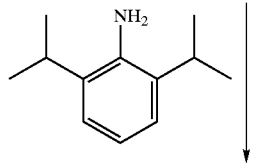

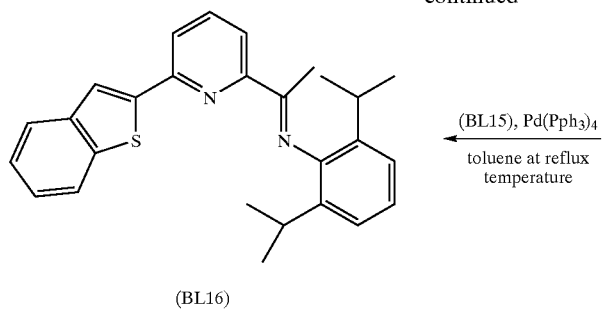

(BL16)

(BL15), Pd(Pph₃)₄ toluene at reflux temperature

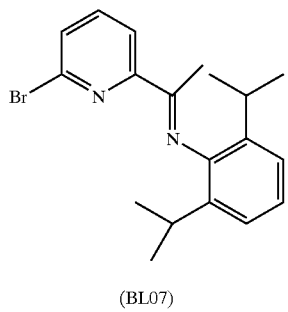

(BL07)

Synthesis of (BL15)

13.1 ml of BuLi 1.6 M in hexane (21.0 mmoles), are added dropwise, at 0° C. and in about 15', to a solution of 2.486 g (20.0 mmoles) of benzothiophene in 50 ml of THF. The whole mixture is left under stirring at room temperature for 10', and is then brought to reflux temperature. After 45' the mixture is cooled to −78°, 4.38 g (22.0 mmoles) of solid $(CH_3)_3SnCl$ are added and the mixture is left under stirring, at this temperature for 1 h.

The mixture is then rapidly brought to room temperature, diluted with 100 ml of $CH_2Cl_2$, washed with 2×50 ml of $H_2O$, 2×50 ml of a saturated solution of $NaHCO_3$ and again with 2×50 ml of $H_2O$.

The organic phase is anhydrified with $Na_2SO_4$ and, on removing the solvent at reduced pressure, 5.10 g (17.0 mmoles, yield 85%) of (BL15) are obtained as a limpid light orange-coloured oil.

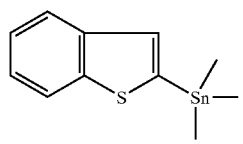

(BL15)

$C_{11}H_{14}SSn$.
FW 296.99 g mol⁻¹.
¹H NMR (CDCl₃) δ=0.55 (s, 9H, Sn(C$\underline{H}_3$)₃); 7.34–7.47 (m, 2H, C$\underline{H}$ Ar); 7.53 (s, 1H, C$\underline{H}$ Ar); 7.90–8.02 (m, 2H, C$\underline{H}$ Ar).
¹³C NMR (CDCl₃): δ=−7.54 (9C; Sn($\underline{C}H_3$)₃); 122.71 (1C, $\underline{C}$H Ar); 123.60 (1C, $\underline{C}$H Ar); 124.31 (1C, $\underline{C}$H Ar); 124.63 (1C, $\underline{C}$H Ar); 132.69 (1C, $\underline{C}$H Ar); 141.12 (1C, $\underline{C}$ Ar); 141.78 (1C, $\underline{C}$ Ar); 144.98 (1C, $\underline{C}$ Ar).

Synthesis of BL02

A solution of 7.107 g (30.00 mmoles) of 2,6-dibromopyridine in 130 ml of dist. $Et_2O$ is cooled, under a stream of $N_2$ to −78° C. and 18.8 ml (30.0 mmoles) of a solution 1.6 M of BuLi in hexane are added dropwise, in about 20'. After 30' 3.1 ml (33.0 mmoles) of N,N-dimethyl-acetamide are added and the mixture is left under stirring for 1 h and 15'. The mixture is slowly brought to room temperature, 40 ml of HCl 1N are added and the two phases are separated. The aqueous phase is extracted with $Et_2O$ (3×30 ml) and the organic phases anhydrified with $Na_2SO_4$. The solution is then concentrated to a volume of about 10–12 ml and brought to 0° C.

After 12 h the crystals thus obtained are filtered and 4.061 g (21.60 mmoles) of BL02 are obtained.

1-(6-Bromopyridin-2-yl)-ethanone*

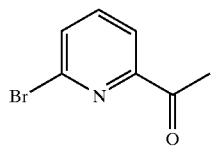

Yield 72%.
F.W. 200.03 g mol⁻¹.
m.p. 44° C.
IR: $\nu_{(C=O)}$ 1695 cm⁻¹.
¹H NMR (CDCl₃): δ=2.7 (s, 3H, Ar—C(O)C$\underline{H}_3$); 7.6 (m, 2H, C$\underline{H}$ Ar.); 8.0 (dd, J=6.5, 2.1 Hz, 1H, C$\underline{H}$ Ar.).
¹³C NMR (CDCl₃): δ=26.4 (1C; Ar—C(O)$\underline{C}H_3$); 121.1 (1C, $\underline{C}H$ Ar.); 132.4 (1C, $\underline{C}H$ Ar.); 139.8 (1C, $\underline{C}H$ Ar.); 142.0 (1C, $\underline{C}H$ Ar.); 154.9 (1C, $\underline{C}H$ Ar.); 198.5 (1C, Ar—$\underline{C}(O)CH_3$).

* Ref: C. Bolm, M. Ewald, M. Felder, G. Schlingloff Chem. Ber. 1992, 125, 1169–1190.

Synthesis of BL07

0.60 g (3.0 mmoles) of BL02 and 1.77 g (pure tech. at 90%, 9.0 mmoles) of 2,6-diisopropylaniline are brought, without a solvent, to 105–110° C. After 16 h IR analysis reveals that the reaction has finished: a small amount of $CH_2Cl_2$ is added to the oily brown residue, which is then crystallized from $CH_3OH$.

0.930 g (2.59 mmoles. yield 86%) of BL07 are obtained as yellow crystals.

N-[(E)-1-(6-bromo-2-pyridinyl)ethylidene]-2,6-diisopropyl-aniline or N-[(E)-1-(6-bromo-2-pyridinyl)ethylidene]-N-(2,6-diisopropylphenyl)amine

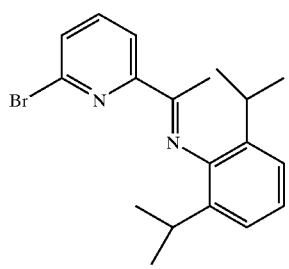

(BL07)

F.W. 359.32 g mol⁻¹.
m.p. 126–128° C.
IR: $\nu_{(C=N)}$ 1639 cm⁻¹.
¹H NMR (CDCl₃): δ=1.15 (d, J=6.8 Hz, 6H, CH(C$\underline{H}_3$)(CH₃)); 1.15 (d, J=6.9 Hz, 6H, CH(CH₃)(C$\underline{H}_3$)); 2.20 (s, 3H, C(N—Ar) CH₃); 2.64–2.77 (m, 2H, CH(CH₃)₂); 7.06–7.20 (m, 3H, CH Ar.); 7.59 (dd, J=7.96, 1.3 Hz, 1H, CH Ar.); 7.65–7.72 (m, 1H, CH Ar.); 8.33 (dd, 1H, CH Ar., J=7.5, 1.3 Hz).

$^{13}$C NMR (CDCl₃): δ=17.98 (1C, C(N—Ar)CH₃); 23.55 (2C, CH—CH₃); 23.90 (2C, CH—CH₃); 28.97 (2C, CH—(CH₃)₂); 120.73 (1C, CH Ar.); 123.72 (2C, CH Ar.); 124.50 (1C, CH Ar.); 129.89 (1C, CH Ar.); 136.34 (1C, C Ar.); 139.46 (1C, CH Ar.); 141.68 (1C, CH Ar.); 146.80 (1C, C Ar.); 158.09 (1C, CH Ar.); 166.62 (1C, C(N—Ar)CH₃).

Synthesis of the Ligand BL16

0.055 g (0.047 mmoles) of Pd(Pph₃)₄ are added to a deaerated solution of 0.85 g (2.36 mmoles) of BL07 and 0.70 g (2.36 mmoles) of BL15 in 10 ml of toluene, and the mixture is brought to reflux temperature. After 2 h GC-MS analysis shows the disappearance of the starting reagents. The solvent is evaporated at reduced pressure and a minimum quantity of CH₂Cl₂ is added to the solid yellow residue thus obtained, which is crystallized from CH₂Cl₂/CH₃OH.

0.84 g (2.04 mmoles, yield 86%) of BL16 are obtained as yellow crystals.

N-{(E)-1-[6-(1-benzothiophen-2-yl)-2-pyridinyl]ethylidene}-2,6-diisopropylaniline or
N-{(E)-1-[6-(1-benzothiophen-2-yl)-2-pyridinyl]ethylidene}-N-(2,6-diisopropylphenyl)amine

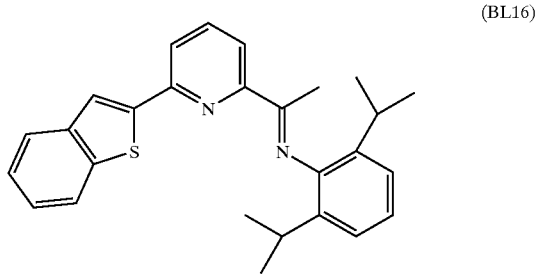

(BL16)

C₂₇H₂₈N₂S.

F.W. 412.72 g mol⁻¹.

m.p. 171–172° C.

IR: $v_{(C=N)}$ 1643 cm⁻¹.

$^{1}$H NMR (CDCl₃): δ=1.19 (d, J=6.7 Hz, 6H, CH(CH₃) (CH₃)); 1.20 (d, J=7.0 Hz, 6H, CH(CH₃) (CH₃)); 2.35 (s, 3H, Ar—C(N—Ar) CH₃); 2.80 (m, 2H, CH(CH₃)₂); 7.10–7.25 (m, 3H, CH arom); 7.37–7.41 (m, 2H, CH arom); 7.83–7.93 (m, 5H, CH arom); 8.33 (dd, 1H, CH arom, J=6.5, 2.4 Hz).

$^{13}$C NMR (CDCl₃): δ=17.94 (1C, Ar—C(N—R)CH₃); 23.71 (2C, CH(CH₃) (CH₃); 24.02 (2C, CH(CH₃) (CH₃); 29.07 (2C, CH—(CH₃) (CH₃); 120.73 (1C, CH Ar.); 121.01 (1C, CH Ar.); 121.86 (1C, CH Ar.); 123.29 (1C, CH Ar.); 123.79 (2C, CH Ar.); 124.42 (1C, CH Ar.); 124.91 (1C, CH Ar.); 125.27 (1C, CH Ar.); 125.84 (1C, CH Ar.); 136.54 (2C, C Ar.); 137.85 (1C, CH Ar.); 141.30 (1C, C Ar.); 141.55 (1C, C Ar.); 145.81 (1C, C Ar.); 147.25 (1C, C Ar.); 152.09 (1C, C Ar.); 156.72 (1C, C Ar.); 167.64 (1C, Ar—C(N—R) CH₃).

Example 2

Synthesis of the Ligand Having General Formula (I) Called (BL14)

The reaction scheme (see scheme 2) is very similar to that of Example 1. The only difference is that the reaction starts from 2-(9-anthryl)thiophene (BL12) instead of benzothiophene.

Scheme 2

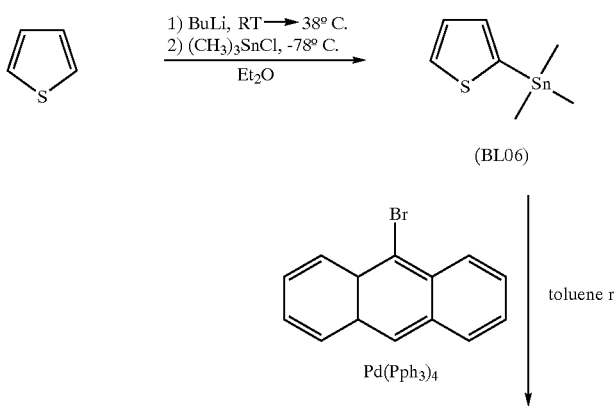

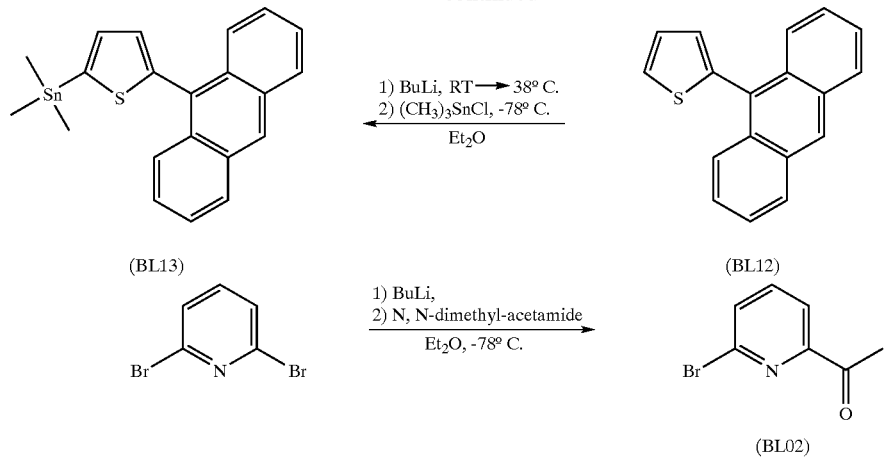

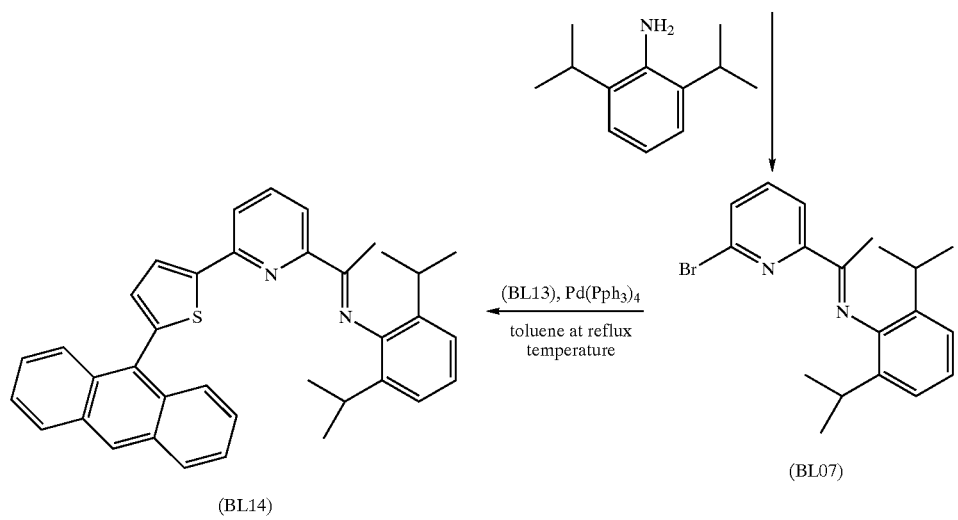

Synthesis of BL12

2-(9-anthryl)thiophene

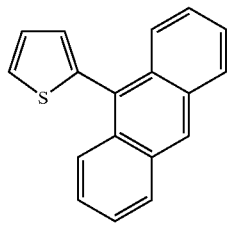

(BL12)

0.069 g (0.06 mmoles) of Pd(Pph$_3$)$_4$ are added to a deaerated solution of 0.771 g (3.0 mmoles) of 9-bromo-anthracene and 0.74 g (3.0 mmoles) of BL06 in 10 ml of toluene, and the mixture is brought to reflux temperature. After 28 h GC-MS analysis shows the disappearance of the starting reagents. The mixture is diluted with 30 ml of CH$_2$Cl$_2$, washed with 2×30 ml of H$_2$O, 2×30 ml of a saturated solution of NaHCO$_3$ and again with 2×30 ml of H$_2$O. The organic phase is anhydrified with Na$_2$SO$_4$ and upon evaporation of the solvent at reduces pressure, a yellow-orange solid residue is obtained, which is purified by flash chromatography (SiO$_2$, eluant petroleum ether, r$_f$=0.25).

0.59 (2.27 mmoles), yield 76%) of BL12 are obtained as a yellow solid.

C$_{18}$H$_{12}$S.
F.W. 260.36 g mol$^{-1}$.
m.p. 111–113° C.
$^1$H NMR (CDCl$_3$): δ=7.21 (dd, J=3.4, 1.2 Hz, 1H, CH Ar.); 7.33 (dd, J=5.1, 3.4 Hz, 1H, CH Ar.); 7.38–7.54 (m, 4H, CH Ar.); 7.62 (dd, J=5.1, 1.2 Hz, 1H, CH Ar.); 7.84–7.94 (m, 2H, CH Ar.); 8.01–8.13 (m, 2H, CH Ar.); 8.55 (s, 1H, CH Ar.).
$^{13}$C NMR (CDCl$_3$): δ=126.00 (2C, CH Ar.); 126.65 (2C, CH Ar.); 127.35 (2C, CH Ar.); 127.41 (1C, CH Ar.); 127.94 (1C, CH Ar.); 128.72 (1C, CH Ar.); 129.06 (2C, CH Ar.);

129.48 (1C, C Ar.); 130.13 (1C, CH Ar.); 131.97 (2C, C Ar.); 132.65 (2C, C Ar.); 139.71 (1C, C Ar.).

Synthesis of BL 13

Anhydrous glassware, all the operations are carried out under N$_2$.

1.2 ml of BuLi 1.6 M in hexane (1.9 mmoles), are added dropwise, in about 15', to a solution of 0.40 g (1.53 mmoles) of BL12 in 50 ml of THF. The whole mixture is left under stirring at room temperature for 10', and is then brought to reflux temperature. After 45' the mixture is cooled to −78°, 0.372 g (1.9 mmoles) of solid (CH$_3$)$_3$SnCl are added and the mixture is left under stirring, at this temperature for 1 h.

The mixture is then rapidly brought to room temperature, diluted with 100 ml of CH$_2$Cl$_2$, washed with 2×50 ml of H$_2$O, 2×50 ml of a saturated solution of NaHCO$_3$ and again with 2×50 ml of H$_2$O.

The organic phase is anhydrified with Na$_2$SO$_4$ and, on removing the solvent at reduced pressure, 0.49 g (1.16 mmoles, yield 76%) of (BL13) are obtained as an orange-coloured oil.

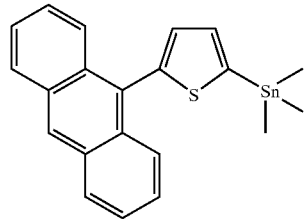
(BL13)

C$_{21}$H$_{20}$SSn.
FW 423.15.
$^1$H NMR (CDCl$_3$): δ=0.48 (s, 9H, Sn(CH$_3$)$_3$); 7.31 (d, J=3.2 Hz, 1H, CH Ar.); 7.38–7.52 (m, 5H, CH Ar.); 7.86–7.90 (m, 2H, CH Ar.); 8.02–8.07(m, 2H, CH Ar.); 8.52 (s, 1H, CH Ar.).
$^{13}$C NMR (CDCl$_3$): δ=−7.36 (3C; Sn(CH$_3$)$_3$); 125.86 (2C, CH Ar.); 126.34 (2C, CH Ar.); 127.44 (2C, CH Ar.); 128.26 (1C, CH Ar.); 128.91 (2C, CH Ar.); 130.14 (1C, C Ar.); 131.34 (1C, C Ar.); 131.89 (2C, CH Ar.); 132.29 (2C, C Ar.); 135.78 (1C, C Ar.); 139.72 (1C, C Ar.); 145.31 (1C, C Ar.).

Synthesis of BL02

See the procedure described in Example 1.

Synthesis of BL07

See the procedure described in Example 1.

Synthesis of the Ligand BL14

0.024 g (0.02 mmoles) of Pd(Pph$_3$)$_4$ are added to a deaerated solution of 0.45 g (1.06 mmoles) of BL07 and 0.38 g (1.06 mmoles) of BL13 in 10 ml of toluene, and the mixture is brought to reflux temperature. After 18 h the solvent is evaporated at reduced pressure and a minimum quantity of CH$_2$Cl$_2$ is added to the oily residue thus obtained, which is crystallized from CH$_2$Cl$_2$/CH$_3$OH.

0.35 g (0.65 mmoles, yield 61%) of BL14 are obtained as yellow-beige crystals.

N-(2,6-diisopropylphenyl)-N-((E)-1-{6-[5-(9-anthryl)-2-thienyl]-2-pyridinyl}ethylidene)aniline or
N-(2,6-diisopropylphenyl)-N-((E)-1-{6-[5-(9-anthryl)-2-thienyl]-2-pyridinyl}ethylidene)-N-phenylamine

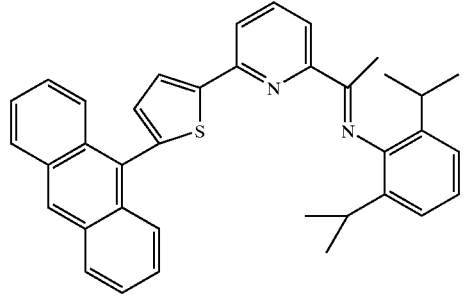
(BL14)

C$_{37}$H$_{34}$N$_2$S.
m.p. 243–244° C.
IR: ν$_{(C=N)}$ 1643 cm$^{-1}$.
F.W. 538.88 g mol$^{-1}$.
$^1$H NMR (CDCl$_3$): δ=1.14 (d, J=6.9 Hz, 6H, CH(CH$_3$)(CH$_3$)); 1.17 (d, J=6.8 Hz, 6H, CH(CH$_3$) (CH$_3$)); 2.23 (s, 3H, Ar—C(N—R) CH$_3$); 2.70–2.84 (m, 2H, CH(CH$_3$)); 7.05–7.20 (m, 3H, CH Ar.); 7.23 (d, J=3.6 Hz, 1H, CH Ar.); 7.41–7.53 (m, 4H, CH Ar.); 7.86–7.90 (m, 3H, CH Ar.); 8.29 (dd, J=5.3, 3.3 Hz, 1H, CH Ar.); 8.56 (s, 1H, CH Ar.).
$^{13}$C NMR (CDCl$_3$): δ=17.78 (1C, Ar—C(N—R)CH$_3$); 23.58 (2C, CH(CH$_3$) (CH$_3$); 23.90 (2C, CH(CH$_3$) (CH$_3$); 28.93 (2C, CH(CH$_3$) (CH$_3$); 119.93 (1C, CH Ar.); 120.02 (1C, CH Ar.); 123.64 (2C, CH Ar.); 124.21 (1C, CH Ar.); 125.32 (1C, CH Ar.); 125.98 (2C, CH Ar.); 126.69 (2C, CH Ar.); 127.19 (2C, CH Ar.); 128.81 (1C, CH Ar.); 129.03 (2C, CH Ar.); 131.27 (1C, CH Ar.); 131.88 (2C, C Ar.); 132.30 (2C, C Ar.); 136.45 (2C, C Ar.); 137.96 (1C, CH Ar.); 142.25 (1C, C Ar.); 146.86 (1C, C Ar.); 147.17 (1C, C Ar.); 152.08 (1C, C Ar.); 156.65 (1C, C Ar.); 167.63 (1C, Ar—C(N—R)CH$_3$).

Example 3

Synthesis of the Ligand Having General Formula (I) Called (BL08)

The reaction scheme (Scheme 3) is very similar to that of Example 2. The only difference is in the use of thiophene instead of 2-(9-anthryl)thiophene.

Scheme 3

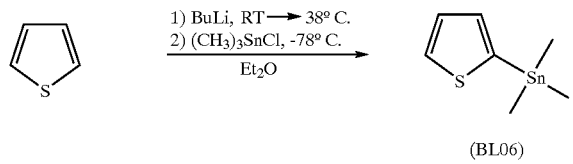
(BL06)

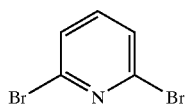 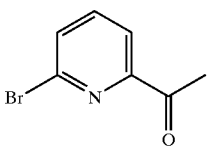

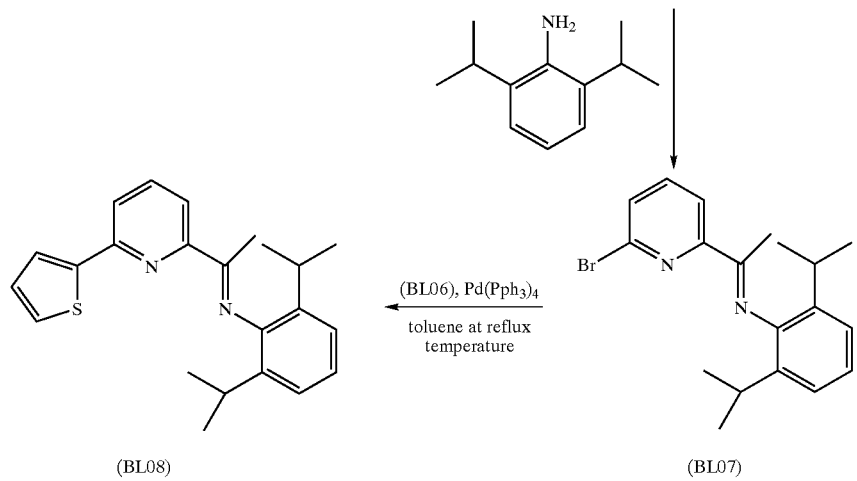

Synthesis of BL06

Anhydrous glassware, all the operations are carried out under $N_2$.

7.5 ml (12.0 mmoles) of BuLi 1.6 M in hexane are added dropwise, at room temperature, in about 15', to a solution of 0.840 g (10.0 mmoles) of thiophene in 15 ml of anhydrous $Et_2O$. The mixture is brought to reflux temperature (the colour of the solution changes from yellow to mud brown) and, after 30' is cooled to −78° and 2.39 g (12.0 mmoles) of $(CH_3)_3SnCl$ are added. After 1.1 h the bath at −78° C. is removed and the mixture is left to slowly rise to room temperature. The resulting suspension is washed with 30 ml of $H_2O$, 30 ml of a saturated solution of $NaHCO_3$, again with 2×30 ml of $H_2O$ and is anhydrified with $Na_2SO_4$. Upon evaporation of the solvent at reduced pressure, 2.33 g (9.44 mmoles, yield 94%) of BL06 are obtained as an orange oil which can be used without further purification.

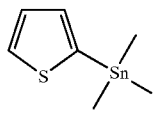

(BL06)

$^1$H NMR (CDCl$_3$): δ=0.53 (s, 9H, Sn(C$\underline{H}_3$)$_3$); 7.28–7.38 (m, 2H, C$\underline{H}$ Ar.); 7.72 (dd, 1H, C$\underline{H}$ Ar., $J_1$=4.4 Hz, $J_2$=1.0 Hz).

$^{13}$C NMR (CDCl$_3$): δ=−7.62 (9C; Sn($\underline{C}$H$_3$)$_3$); 128.68 (1C, $\underline{C}$H Ar.); 131.49 (1C, $\underline{C}$H Ar.); 135.72 (1C, $\underline{C}$H Ar.); 137.84 (1C, $\underline{C}$ Ar.).

Synthesis of BL02
See the procedure described in Example 1.

Synthesis of BL07
See the procedure described in Example 1.

Synthesis of the Ligand BL08

0.359 g (F.W. 359.44, 1.00 mmole) of BL07 and 0.247 g (F.W. 246.93, 1.00 mmole) of BL06 are dissolved in 5 ml of toluene and the resulting solution is deaerated in a stream of $N_2$. 0.030 g (F.W. 1155.58, 0.026 mmoles) of Pd(Pph$_3$)$_4$ are then added and the mixture is brought to reflux temperature. After 2 h it is brought to room temperature and the brown solid present in suspension is filtered. Upon evaporation of the solvent, a yellow crystalline solid is obtained, which is washed with 2×30 ml of methanol.

0.23 g of BL08 are obtained (0.64 mmoles, yield 64%).

N-(2,6-diisopropylphenyl)-N-{(E)-1-[6-(2-thienyl)-2-pyridinyl]ethylidene} amine or
2,6-diisopropyl-N-{(E)-1-[6-(2-thienyl)-2-pyridinyl]ethylidene} aniline.

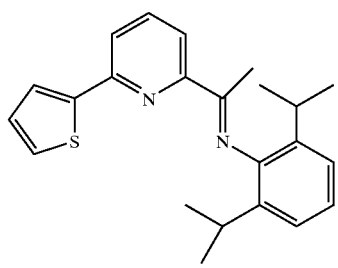

(BL08)

$C_{23}H_{26}N_2S$.
F.W. 362.66 g mol$^{-1}$.
m.p. 140° C.
IR: $\nu_{(C=N)}$ 1641 cm$^{-1}$.
$^1$H NMR (CDCl$_3$): δ=1.13–1.20 (m, 12H, CH(C$\underline{H}_3$)$_2$); 2.29 (s, 3H, Ar—C$\underline{H}_3$); 2.66–2.98 (m, 2H, C$\underline{H}$(CH$_3$)$_2$); 7.06–7.23 (m, 4H, C$\underline{H}$ arom); 7.42 (dd, J=5.0, 1.1 Hz, 1H, C$\underline{H}$ arom); 7.67 (dd, J=3.7, 1.1 Hz, 1H, C$\underline{H}$ arom); 7.75 (dd, J=7.9, 1.5 Hz, 1H, C$\underline{H}$ Ar.); 7.79–7.87 (m, 1H, C$\underline{H}$ arom); 8.25 (dd, J=7.4, 1.5 Hz, 1H, C$\underline{H}$ arom).
$^{13}$C NMR (CDCl$_3$): δ=17.85 (1C, Ar—C(N—R)$\underline{C}$H$_3$); 23.64 (2C, CH($\underline{C}$H$_3$) (CH$_3$); 23.94 (2C, CH(CH$_3$) ($\underline{C}$H$_3$); 28.99 (2C, $\underline{C}$H(CH$_3$) (CH$_3$); 119.97 (1C, $\underline{C}$H Ar.); 120.21 (1C, $\underline{C}$H Ar.); 123.70 (2C, $\underline{C}$H Ar.); 124.26 (1C, $\underline{C}$H Ar.); 125.32 (1C, $\underline{C}$H Ar.); 128.41 (1C, $\underline{C}$H Ar.); 128.79 (1C, $\underline{C}$H Ar.); 136.51 (2C, $\underline{C}$ Ar.); 137.86 (1C, $\underline{C}$H Ar.); 145.73 (1C, $\underline{C}$ Ar.); 147.21 (1C, $\underline{C}$ Ar.); 152.15 (1C, $\underline{C}$ Ar.); 156.57 (1C, $\underline{C}$ Ar.); 167.70 (1C, Ar—$\underline{C}$(N—R)CH$_3$).

Example 4

Synthesis of the Ligand (BL18)

The reaction scheme (see scheme 4) is very similar to that of Example 3.
The starting product is 2-ethyl thiophene instead of thiophene.

Synthesis of BL17

Anhydrous glassware, all the operations are carried out under N$_2$.

13.1 ml of BuLi 1.6 M in hexane (21.0 mmoles), are added dropwise, in about 15', to a solution of 2.26 ml (2.24 g, 20.0 mmoles) of 2-ethyl-thiophene in 60 ml of THF. The whole mixture is left under stirring at room temperature for 10', and is then brought to reflux temperature. After 45' the mixture is cooled to −78°, 4.38 g (22.0 mmoles) of solid (CH$_3$)$_3$SnCl are added and the mixture is left under stirring, at this temperature for 1 h.

The mixture is then rapidly brought to room temperature, diluted with 100 ml of CH$_1$C$_2$, washed with 2×50 ml of H$_2$O, 2×50 ml of a saturated solution of NaHCO$_3$ and again with 2×50 ml of H$_2$O.

The organic phase is anhydrified with Na$_2$SO$_4$ and, on removing the solvent at reduced pressure, 5.28 g (19.2 mmoles, yield 96%) of (BL17) are obtained as a limpid orange oil.

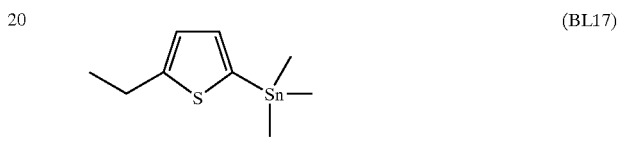
(BL17)

$C_9H_{16}SSn$.
FW 274.99 g mol$^{-1}$.

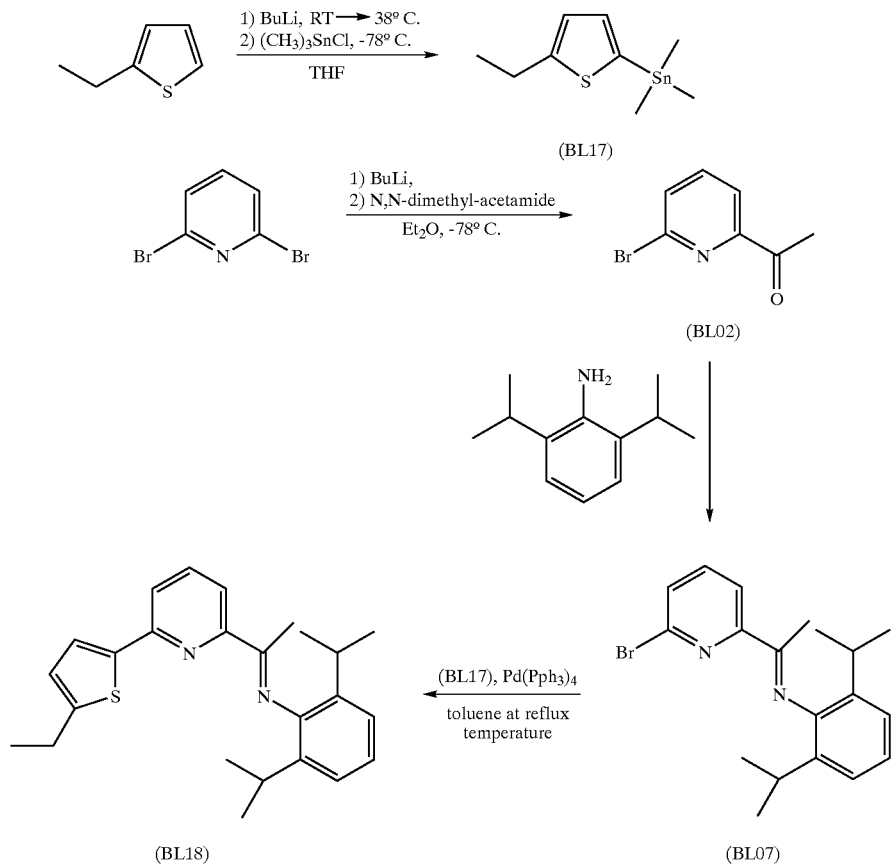

$^1$H NMR (CDCl$_3$): δ=0.40 (s, 9H, Sn(C$\underline{H}_3$)$_3$); 1.38 (t, J=7.4, 3H, CH$_2$—C$\underline{H}_3$); 2.95 (qd, J=7.4, 0.9 Hz, 2H, C$\underline{H}_2$—CH$_3$); 6.97 (dt, J=3.2, 0.9, 1H, C$\underline{H}$ Ar.); 7.08 (d, J=3.2 Hz, 1H, C$\underline{H}$ Ar.).

$^{13}$C NMR (CDCl$_3$): δ=−7.63 (3C; Sn($\underline{C}$H$_3$)$_3$); 16.82 (1C, CH$_2$—CH$_3$); 23.98 (1C, $\underline{C}$H$_2$—CH$_3$); 125.50 (1C, C$\underline{H}$ Ar.); 135.31 (1C, $\underline{C}$ Ar.); 135.79 (1C, $\underline{C}$H Ar.); 154.09 (1C, $\underline{C}$ Ar.).

Synthesis of BL02

See the procedure described in Example 1.

Synthesis of BL07

See the procedure described in Example 1.

Synthesis of BL18

0.552 g (2.0 mmoles) of BL17 and 0.72 g (2.0 mmoles) of BL07 are dissolved in 8 ml of toluene and the resulting solution is deaerated in a stream of N$_2$. 0.046 g (0.0 mmoles) of Pd(Pph$_3$)$_4$ are then added and the mixture is brought to reflux temperature. After 4 h it is brought to room temperature and the brown solid present in suspension is filtered. Upon evaporation of the solvent, an oily residue is obtained to which 5 ml of CH$_2$Cl$_2$ are added and the mixture is crystallized from CH$_3$OH.

1$^{st}$ crop 0.38 g (0.98 mmoles, yield 49%)
2$^{nd}$ crop 0.26 g (0.67 mmoles, yield 33%)
Total: 0.64 g, overall yield 82%, of (BL18)
N-{(E)-1-[6-(5-ethyl-2-thienyl)-2-pyridinyl]ethylidene}-2,6-diisopropylaniline or
N-(2,6-diisopropylphenyl)-N-{(E)-1-[6-(5-ethyl-2-thienyl)-2-pyridinyl]ethylidene} amine

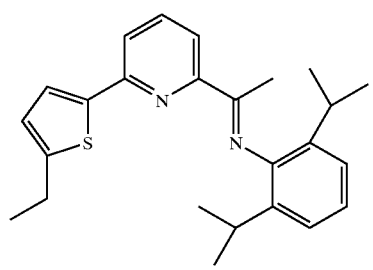

(BL18)

C$_{25}$H$_{30}$N$_2$S.
F.W. 390.73 g mol$^{-1}$.
m.p. 121° C.
IR: ν$_{(C=N)}$ 1646 cm$^{-1}$.
$^1$H NMR (CDCl$_3$): δ=1.16 (d, J=6.9, 12H, CH(C$\underline{H}_3$)$_2$); 1.37 (t, J=7.5, 3H, CH$_2$—CH$_3$); 2.29 (s, 3H, Ar—C$\underline{H}_3$); 2.77 (sept, 2H, C$\underline{H}$(CH$_3$)$_2$); 2.90 (q, J=7.5, 2H, C$\underline{H}_2$—CH$_3$); 6.83 (d, J=3.6 Hz, 1H, CH Ar.); 7.06–7.21 (m, 3H, C$\underline{H}$ arom); 7.48 (d, J=3.6, 1H, CH Ar.); 7.68 (dd, J=7.7, 0.9 Hz, 1H, C$\underline{H}$ arom.); 7.75–7.82 (m, 1H, C$\underline{H}$ arom); 8.20 (dd, J=7.6, 0.9 Hz, 1H, C$\underline{H}$ arom).

$^{13}$C NMR (CDCl$_3$): δ=16.61 (1C, CH$_2$—$\underline{C}$H$_3$); 17.85 (1C, Ar—C(N—R)$\underline{C}$H$_3$); 23.61 (2C, CH($\underline{C}$H$_3$) (CH$_3$); 23.90 (2C, CH(CH$_3$) ($\underline{C}$H$_3$); 24.49 (1C, $\underline{C}$H$_2$—CH$_3$); 28.92 (2C, $\underline{C}$H(CH$_3$) (CH$_3$)); 119.42 (1C, $\underline{C}$H Ar.); 119.71 (1C, $\underline{C}$H Ar.); 123.64 (2C, $\underline{C}$H Ar.); 124.17 (1C, $\underline{C}$H Ar.); 125.22 (2C, $\underline{C}$H Ar.); 136.51 (2C, $\underline{C}$ Ar.); 137.86 (1C, $\underline{C}$H Ar.); 142.78 (1C, $\underline{C}$ Ar.); 147.24 (1C, $\underline{C}$ Ar.); 150.99 (1C, $\underline{C}$ Ar.); 152.42 (1C, $\underline{C}$ Ar.); 156.45 (1C, $\underline{C}$ Ar.); 167.74 (1C, Ar—$\underline{C}$(N—R)CH$_3$).

Example A

Synthesis of the Complex BC03 Starting from the Ligand BL08

10 ml of distilled and deaerated n-butanol are brought to reflux temperature, 0.295 g (1.24 mmoles) of CoCl$_2$.6H$_2$O are dissolved therein, under a stream of nitrogen, and the solvent is distilled to a total volume of the solution of about 7–8 ml. 0.450 g (1.24 mmoles) of (BL08) are then added and the mixture is slowly brought to room temperature.

The green crystalline precipitate is filtered, washed with n-butanol, then with n-hexane previously deaerated and is finally transferred to a Schlenk tube.

0.58 g (1.18 mmoles; yield 95%) of BC03 are obtained as a green microcrystalline solid.

| Reagents | F.W. (g mol$^{-1}$) | molar ratio | mmoles | grams |
|---|---|---|---|---|
| BL08 | 362.66 | 1 | 1.24 | 0.450 |
| CoCl$_2$.6H$_2$O | 237.93 | 1 | 1.24 | 0.295 |
| BC03 | | | | |

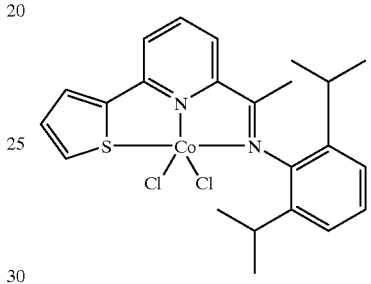

FW 492.50 g mol$^{-1}$.

Example B

Synthesis of the Complex BC04 Starting from the Ligand BL08

| Products | F.W. (g mol$^{-1}$) | molar ratio | mmoles | grams |
|---|---|---|---|---|
| BL08 | 362.66 | 1 | 1.24 | 0.450 |
| FeCl$_2$.4H$_2$O | 198.82 | 1 | 1.24 | 0.247 |

0.50 g (1.02 mmoles; yield 82%) of BC04 are obtained as a red microcrystalline solid.

(BC04)

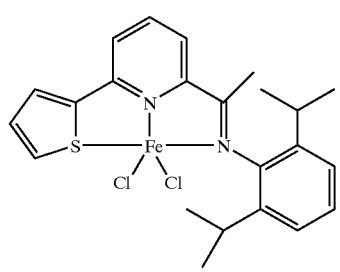

FW 489.41 g mol$^{-1}$.

Example C

Synthesis of the Complex BC05 Starting from the Ligand BL18

| Products | F.W. (g mol$^{-1}$) | molar ratio | mmoles | grams |
|---|---|---|---|---|
| BL18 | 390.73 | 1 | 0.51 | 0.200 |
| CoCl$_2$.6H$_2$O | 237.93 | 1 | 0.51 | 0.116 |

0.207 g (0.40 mmoles; yield 78%) of BC05 are obtained as a green microcrystalline solid.

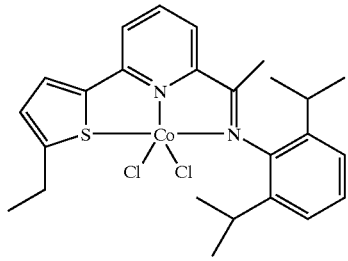

(BC05)

FW 520.57 g mol$^{-1}$.

Example D

Synthesis of the Complex BC07 Starting from the Ligand BL16

| Products | F.W. (g mol$^{-1}$) | molar ratio | mmoles | grams |
|---|---|---|---|---|
| BL16 | 412.72 | 1 | 0.485 | 0.200 |
| COCl$_2$.6H$_2$O | 237.93 | 1 | 0.462 | 0.110 |

0.20 g. (0.37 mmoles; yield 80%) of BC07 are obtained as a green microcrystalline solid.

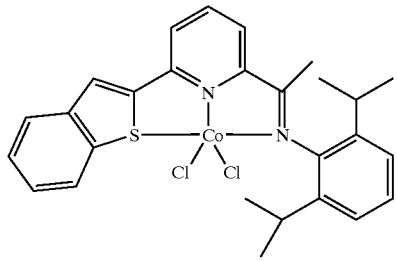

(BC07)

FW 520.57 g mol$^{-1}$.

Example E

Synthesis of the Complex BC09

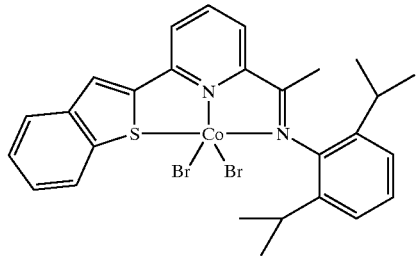

(BC09)

Example Alpha

Complex Supported on Polystyrene 0.53 ml of a 1.5 M solution of LDA in THF are added, at 0° C., to a solution of 0.310 grams of ligand BL18 (FW 390.58 g mol$^{-1}$, 0.794 mmoles) in 20 ml of THF. After 3.5 hours at this temperature, 0.50 grams (0.8 mmoles Cl/g, 0.40 mmoles) of Merrifield chloromethylpolystyrene are added and the mixture is left under stirring at 0° C. for 4 hours and at room temperature for 24 hours. The resin is then filtered, washed with 2×30 ml of THF, 3×30 ml of H$_2$O and 3×30 ml of CH$_2$Cl$_2$ and dried at reduced pressure. 0.35 grams of resin are obtained.

0.28 grams (0.80 mmoles) of CoCl$_2$.6H$_2$O are dissolved in 100 ml of n-butanol at 40° C. and 0.35 grams of the functionalized resin obtained as described above are added. After 30 minutes the mixture is filtered, washed with 2×20 ml of n-butanol, 3×40 ml of petroleum ether and the excess solvent is removed in a stream of N$_2$.

0.41 grams of green solid are obtained.

Example Beta

Complex Supported on Silica

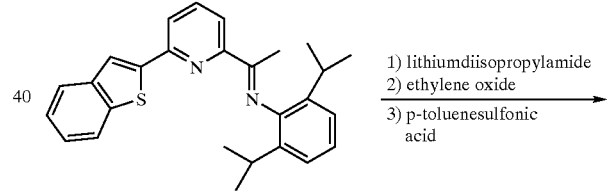

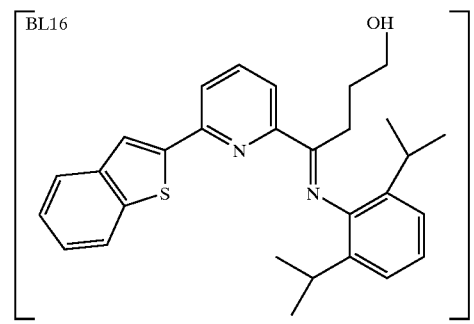

0.80 ml of a 1.5 M solution of lithiumdiisopropylamide in THF are added at 0° C. to a solution of 0.5 g of the ligand BL16 (MW 412.72, 1.21 mmoles) in 20 ml of THF. After 3 hours at this temperature a solution of 0.06 g of ethylene oxide (MW 44.05, 1.36 mmoles) in 10 ml of THF are slowly added. The mixture is left under stirring at 0° C. for 5 hours. At the end, 0.258 g of p-toluenesulfonic acid are added and then 0.29 g (1.2 mmoles) of di(3-isocyanatepropyl)-triethoxysilane dissolved in 30 ml of p-xylene and the resulting mixture is brought to reflux temperature.

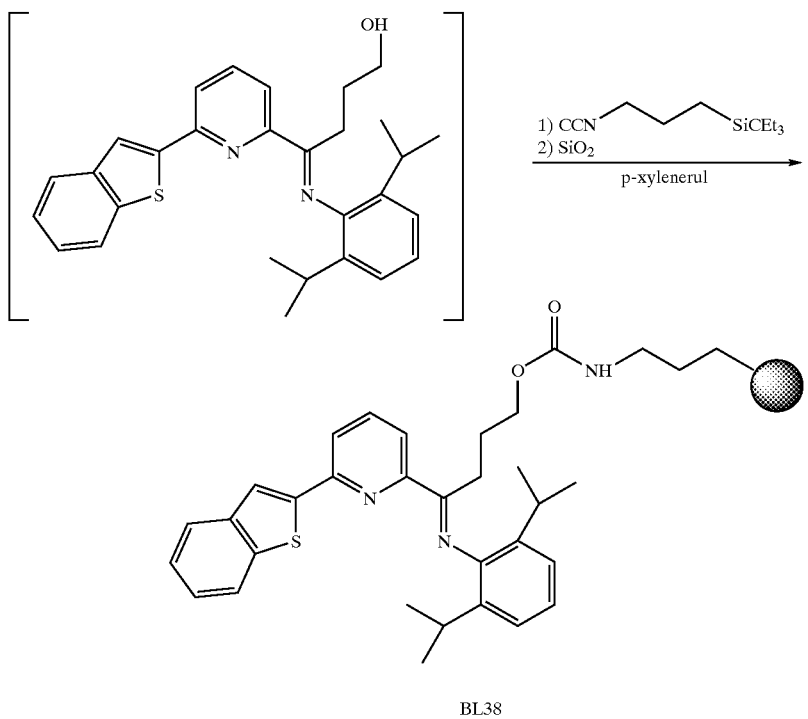

BL38

After 12 hours 3.8 grams of silica are added and after a further 12 hours at reflux temperature the solid present in suspension is filtered, washed with 3×20 ml of p-xylene, 2×30 ml of n-hexane and the residual traces of solvent are eliminated at reduced pressure (40° C.). 4.1 grams of BL38 are obtained.

0.35 ml (1.47 mmoles) of $CoCl_2 \cdot 6H_2O$ are dissolved in 100 ml of n-butanol at 40° C. and 4.1 grams of the functionalized silica prepared above are added.

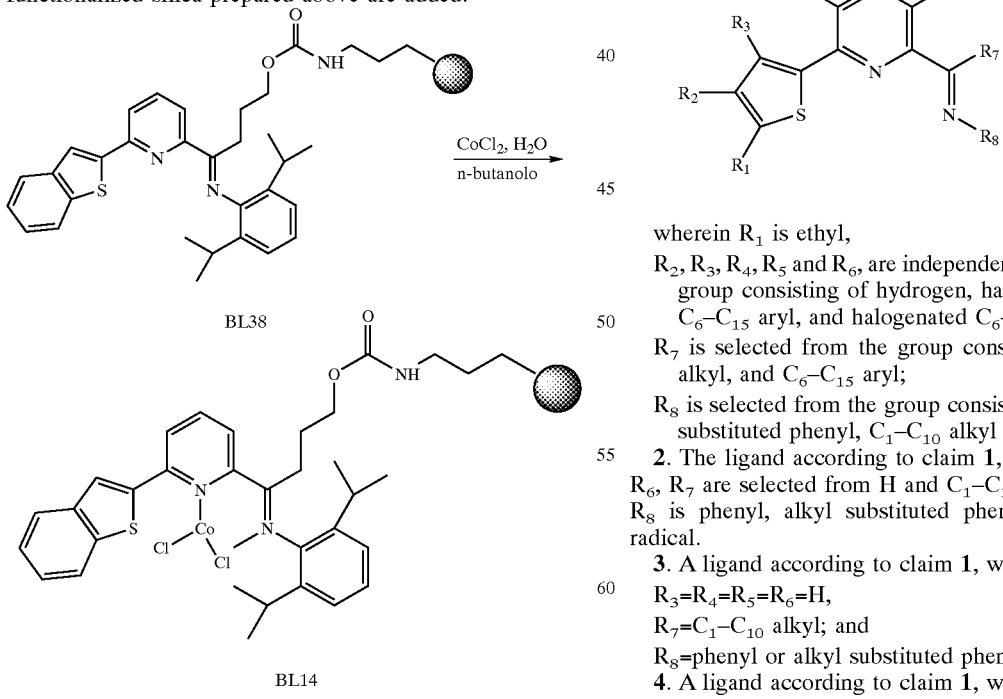

BL38

BL14

After 30 minutes the mixture is filtered, washed with 2×40 ml of n-butanol, 3×50 ml of petroleum ether and the excess solvent is removed in a stream of $N_2$. 4.3 grams of BC14 are obtained as a green solid.

What is claimed is:

1. A ligand represented by formula (I)

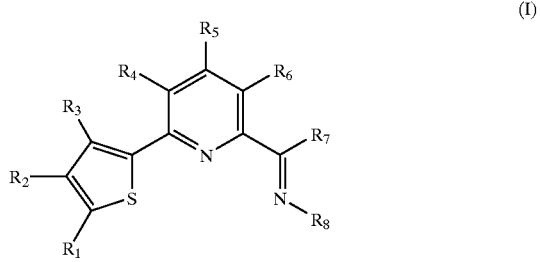

(I)

wherein $R_1$ is ethyl, $R_2$, $R_3$, $R_4$, $R_5$ and $R_6$, are independently selected from the group consisting of hydrogen, halogen, $C_1$–$C_{10}$ alkyl, $C_6$–$C_{15}$ aryl, and halogenated $C_6$–$C_{15}$ aryl;

$R_7$ is selected from the group consisting of H, $C_1$–$C_{10}$ alkyl, and $C_6$–$C_{15}$ aryl;

$R_8$ is selected from the group consisting of phenyl, alkyl substituted phenyl, $C_1$–$C_{10}$ alkyl and $C_6$–$C_{15}$ aryl.

2. The ligand according to claim 1, wherein $R_3$, $R_4$, $R_5$, $R_6$, $R_7$ are selected from H and $C_1$–$C_{10}$ alkyl radicals, and $R_8$ is phenyl, alkyl substituted phenyl, or $C_6$–$C_{15}$ aryl radical.

3. A ligand according to claim 1, wherein
$R_3=R_4=R_5=R_6=H$,
$R_7=C_1$–$C_{10}$ alkyl; and
$R_8$=phenyl or alkyl substituted phenyl.

4. A ligand according to claim 1, wherein
$R_2=R_3=R_4=R_5=R_6=H$,
$R_7=CH_3$; and
$R_8$=2,6-diisopropylphenyl.

5. A process for the preparation of a ligand represented by formula (I)

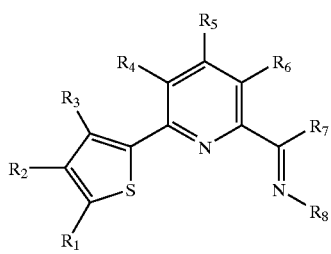

(I)

which comprises:
i) condensing halogen acyl-pyridine having general formula (A),

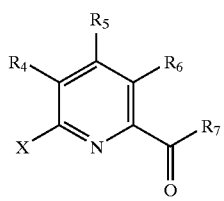

(A)

wherein X is a halogen,
$R_4$, $R_5$ and $R_6$ are independently selected from the group consisting of hydrogen, halogen, $C_1$–$C_{10}$ alkyl, $C_6$–$C_{15}$ aryl, and halogenated $C_6$–$C_{15}$ aryl; and
$R_7$ is selected from the group consisting of H, $C_1$–$C_{10}$ alkyl and $C_6$–$C_{15}$ aryl;
with a primary amine represented by formula (B),

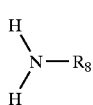

(B)

wherein $R_8$ is selected from the group consisting of phenyl, alkyl substituted phenyl, $C_1$–$C_{10}$ alkyl and $C_6$–$C_{15}$ aryl to produce a halogen imino-pyridine represented by formula (C);

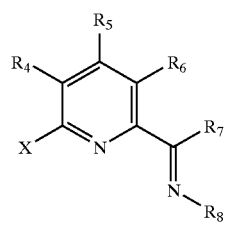

(C)

ii) reacting the halogen imino-pyridine represented by formula (C) with a thiophene derivative represented by formula (D), wherein
$R_1$ is ethyl,
$R_2$ and $R_3$ are independently selected from the group consisting of hydrogen, halogen, $C_1$–$C_{10}$ alkyl, $C_6$–$C_{15}$ aryl, and halogenated $C_6$–$C_{15}$ aryl; and
$R_9$ is an organometallic radical bound to the thiophene ring

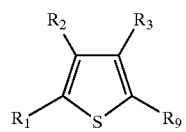

to produce the ligand represented by formula (I).

6. The process according to claim 5, wherein X is Br.

7. The process according to claim 5, wherein the primary amine is an aromatic amine.

8. The process according to claim 5, wherein said organometallic radical is a metal substituted with alkyls wherein the metal is selected from the group consisting of Sn, Li, Mg, Zn and Hg.

9. The process according to claim 5, wherein said organic radical is trimethyl tin.

* * * * *

UNITED STATES PATENT AND TRADEMARK OFFICE
CERTIFICATE OF CORRECTION

PATENT NO. : 6,916,931 B2
DATED : July 12, 2005
INVENTOR(S) : Bianchini et al.

It is certified that error appears in the above-identified patent and that said Letters Patent is hereby corrected as shown below:

<u>Title page,</u>
Item [75], should read:
-- Inventors: Claudio Bianchini, Firenze (IT); Anna Sommazzi, Santa Margherita Ligure (IT); Giuseppe Mantovani, Finale Emilia (IT); Roberto Santi, Novara (IT); Francesco Masi, Sant'Angelo Lodigiano (IT) --.

Signed and Sealed this

Sixth Day of September, 2005

JON W. DUDAS
*Director of the United States Patent and Trademark Office*